US009910030B2

(12) United States Patent
Nirschl et al.

(10) Patent No.: US 9,910,030 B2
(45) Date of Patent: Mar. 6, 2018

(54) BIOCHIP SENSOR

(75) Inventors: Martin Nirschl, Traunstein (DE); Kaori Sugihara, Zürich (CH); Janos Vörös, Zürich (CH); Tomaso Zambelli, Zürich (CH)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 13/346,157

(22) Filed: Jan. 9, 2012

(65) Prior Publication Data
US 2012/0164716 A1 Jun. 28, 2012

Related U.S. Application Data

(63) Continuation of application No. PCT/EP2010/004090, filed on Jul. 7, 2010.

(30) Foreign Application Priority Data

Jul. 7, 2009 (EP) ..................................... 09008858

(51) Int. Cl.
C12M 1/00 (2006.01)
C12M 1/34 (2006.01)
(Continued)

(52) U.S. Cl.
CPC ... G01N 33/5005 (2013.01); G01N 33/48721 (2013.01); G01N 33/5097 (2013.01); G01N 33/525 (2013.01)

(58) Field of Classification Search
CPC ......... G01N 33/48721; G01N 33/5005; G01N 33/5097; G01N 33/525
(Continued)

(56) References Cited

U.S. PATENT DOCUMENTS 3,378,684 A * 4/1968 Mentink ................. B01L 3/508
250/343
7,468,608 B2 12/2008 Feucht et al.
(Continued)

FOREIGN PATENT DOCUMENTS

CN 1566933 A 1/2005
CN 1768262 A 5/2006
(Continued)

OTHER PUBLICATIONS

Thien et al., "Supported planar lipid bilayers (s-BLMs) as electrochemical biosensors", Electrochimica Acta, Elsevier Science Publishers, Barking, GB, vol. 43, No. 23, Jul. 30, 1998, pp. 3587-3610, XP004133579.
(Continued)

Primary Examiner — Nathan Bowers
Assistant Examiner — Lydia Edwards
(74) Attorney, Agent, or Firm — Laurence Greenberg; Werner Stemer; Ralph Locher

(57) ABSTRACT

Small and extremely small molecules and ions or atoms may be detected with the novel device with exceptional sensitivity. The detection is implemented in a simple manner by the known acoustic resonator FBAR or by means of other technologies that measure the physical properties of the filled layer. The permeability of substances (e.g. active ingredients) through membranes such as cell membranes, lipid bilayers, and cell walls can be examined by combining a sensor with the reservoir and the membrane.

11 Claims, 3 Drawing Sheets

(51) Int. Cl.
*C12M 3/00* (2006.01)
*G01N 33/50* (2006.01)
*G01N 33/487* (2006.01)
*G01N 33/52* (2006.01)

(58) Field of Classification Search
USPC ........................................ 435/287.1; 324/633
See application file for complete search history.

(56) References Cited

U.S. PATENT DOCUMENTS

| | | | |
|---|---|---|---|
| 7,498,720 | B2 | 3/2009 | Loebl et al. |
| 7,965,019 | B2* | 6/2011 | Gabl .............................. 310/346 |
| 8,105,820 | B2 | 1/2012 | Brander et al. |
| 2005/0003396 | A1 | 1/2005 | Ozkan et al. |
| 2005/0148065 | A1 | 7/2005 | Zhang et al. |
| 2005/0175501 | A1 | 8/2005 | Thompson et al. |
| 2005/0244487 | A1 | 11/2005 | Sansinena et al. |
| 2006/0009805 | A1 | 1/2006 | Jensen et al. |
| 2006/0125489 | A1* | 6/2006 | Feucht et al. ................. 324/633 |
| 2006/0193748 | A1* | 8/2006 | Tai ........................ G01N 30/34 422/70 |
| 2006/0240540 | A1 | 10/2006 | Nakatsuka |
| 2007/0224639 | A1 | 9/2007 | Matsushita et al. |
| 2008/0026486 | A1* | 1/2008 | Cooper et al. ................. 436/518 |
| 2008/0204043 | A1* | 8/2008 | Wang et al. .................. 324/633 |
| 2008/0220535 | A1* | 9/2008 | LeBoeuf et al. .............. 436/164 |
| 2009/0180350 | A1* | 7/2009 | Dorovsky ................ G01V 1/44 367/35 |
| 2010/0094105 | A1* | 4/2010 | Porat .................... A61K 9/0009 600/309 |
| 2010/0163410 | A1* | 7/2010 | Mastromatteo ...... C12Q 1/6825 204/400 |

FOREIGN PATENT DOCUMENTS

| | | |
|---|---|---|
| CN | 1864063 A | 11/2006 |
| CN | 1892219 A | 1/2007 |
| CN | 1894583 A | 1/2007 |
| CN | 1902497 A | 1/2007 |
| CN | 101246162 A | 8/2008 |
| CN | 101303354 A | 11/2008 |
| DE | 103 08 975 A1 | 2/2004 |
| DE | 103 08 975 B4 | 3/2007 |
| WO | 2006/076008 A2 | 7/2006 |
| WO | 2005064342 A1 | 1/2012 |

OTHER PUBLICATIONS

Cornell, et al., "A biosensor that uses ion-channel switches", Nature, Jun. 1997, pp. 580-583, vol. 387.
Sackmann, et al "Supported Membranes: Scientific and Practical Applications", Science, Jan. 1996, pp. 43-48, vol. 271.
Batsios, G., "Optical Membrane Permeability Sensor", Semester thesis, Jul. 2009, pp. 1-32, ETH Zurich, Zurich, Switzerland.
Kang et al, "A Storable Encapsulated Bilayer Chip Containing a Single Protein Nanopore", J.Am. Chem.Soc., vol. 129, pp. 4701-4705, 2007 (Mar. 22, 2007).

* cited by examiner

BIOCHIP SENSOR

CROSS-REFERENCE TO RELATED APPLICATION

This application is a continuation application, under 35 U.S.C. § 120, of international patent application PCT/EP2010/004090, filed Jul. 7, 2010, which designated the United States; this application also claims the priority, under 35 U.S.C. § 119, of European patent application No. 09008858.4, filed Jul. 7, 2009; the prior applications are herewith incorporated by reference in their entirety.

BACKGROUND OF THE INVENTION

Field of the Invention

The present invention relates to a sensor, in particular a biochip for application in miniaturized laboratories, for instance on so-called lab-on-a-chip cards.

Biochips are devices by means of which the smallest quantities of biological material can be detected and/or examined. For example, biochips allow molecules such as nucleic acids or proteins to be adsorbed onto solid surfaces, and allow automated high-speed parallel analysis of the samples.

A biochip therefore essentially comprises a test panel, a sensor and an electronic evaluation unit, wherein the latter can also be arranged externally and linked to the sensor on the chip by means of connection interfaces.

The test panel is normally characterized by a type of nanoreservoir, which is used for sorption of the sample.

An example of a sensor for a biochip is known from U.S. Pat. No. 7,468,608 B2 and its counterpart German patent DE 103 08 975 B4. There, there is disclosed a thin-film resonator wherein the electrode layer, the piezoelectric layer and the further electrode layer are stacked one above the other. The piezoelectric layer consists of zinc oxide, for example. The top electrode layer (top electrode) is made of gold and comprises the attachment surface for attachment (e.g. adsorption) of the substance of a fluid. The thin-film resonator is attached to a silicon substrate via the bottom electrode layer (bottom electrode). In order to acoustically separate the silicon substrate from the thin-film resonator, e.g. an acoustic mirror is arranged between them, wherein said acoustic mirror has layers of $\lambda/4$ thickness and differing acoustic impedance.

Using the known biochips, it is possible to adsorb substances of relatively high mass, e.g. macromolecules such as proteins or nucleic acids, on the test panels that are routinely used at present. By virtue of their mass, these molecules cause the vibration behavior of the test panel to change, and can be detected accordingly. In the case of small molecules having low mass, this system functions poorly (i.e. resulting in a low level of resolution) or not at all.

Many techniques are known for the detection of smaller molecules, atoms or ions, but none is based on the system of a piezoacoustic thin-film resonator as described in U.S. Pat. No. 7,468,608 B2 and DE 103 08 975, for example.

SUMMARY OF THE INVENTION

It is accordingly an object of the invention to provide a sensor in the form of a biochip which overcomes the above-mentioned disadvantages of the heretofore-known devices and methods of this general type and which provides for further improved sensors such that the mass sensitivity is increased.

With the foregoing and other objects in view there is provided, in accordance with the invention, a biochip, comprising:
  a sensor and a test panel;
  said test panel having a reservoir formed of an absorbent layer and a membrane on top of said absorbent layer, said membrane being at least one membrane selected from the group consisting of a lipid bilayer, a cell, a cell wall, and a cell membrane.

In other words, the objects of the invention are achieved by the subject matter of the invention, which relates to a biochip comprising a sensor and a test panel, wherein the test panel features a reservoir, i.e. an absorbent layer and a membrane thereabove, such that said membrane comprises a lipid bilayer, a cell, a cell wall and/or a cell membrane.

It has been established that cell membranes, cell walls, cells and/or lipid bilayers have a great variety of membrane proteins, which cause the cell adhesion. These membranes have different permeabilities for different substances, such that only certain substances can pass through the membrane, particularly if it still features specific membrane proteins. According to the invention, this effect is utilized for the detection of substances.

There are various paths in the cell membranes, cell walls, lipid bilayers and/or cells for molecules, ions and atoms. These also include e.g. so-called ion channels, which form pores in the membranes, wherein said pores pick up the small molecules such as ions, for example.

Ion channels have been successfully constructed in artificially synthesized lipid bilayers. The cell membrane permeability has been recreated in this way. According to the invention, these lipid bilayers are applied as planar plasma membranes for example to e.g. polymer supports, which both stabilize the membranes and absorb the substance that is to be detected.

According to an advantageous embodiment, the permeability of the membrane is adapted to the substance that must be detected. For example, an ion-selective membrane is used in this case.

The membranes and the polymer supports are selected such that, when the relevant substance penetrates into the membranes and the polymer supports, and is absorbed there, they (only the polymer support, not necessarily the membrane) change their physical properties, such that the substance can be detected. For example, the refractive index, the magnetic induction, the viscosity or the acoustic permeability of the structure can be changed by the presence of the test substance. This change can then be detected by the sensor.

According to an advantageous embodiment, further proteins (so-called membrane proteins) for attaching the relevant molecules or ions are arranged within the membrane.

According to an advantageous embodiment of the invention, the reservoir forms pores. In this case, the porous material is advantageously a polymer, in particular a polyelectrolyte multilayer polymer, a gel or other porous mass such as porous metals or ceramics, e.g. porous silicon, aluminum or similar.

In the case of a PEM polymer support, the PEM is preferably constructed by means of a layer-for-layer method using various polyelectrolytes. For example, polyelectrolytes such as polyetherimide (PEI), polyallylamine (PAH), PGA (polyglutamic acid) or PSS (polystyrol sulfonate) can be used.

According to an advantageous embodiment of the invention, the sensor is an optical, acoustic, magnetic or mechanical sensor, e.g. field-effect transistors, OWL (optical waveguide lightmode) spectroscopy, QCM (quartz crystal microbalance) crystals or GMR (giant magnetoresistance) sensors.

According to a further advantageous embodiment of the invention, the membranes are obtained directly from cells or lipids using DOPS, DOPA or DOPC. These can then be applied directly onto the porous material of the reservoir.

According to an advantageous embodiment, further proteins are introduced into the membrane, wherein these proteins can be introduced by means of proteoliposomes, directly, as a solution or mechanically.

The sensor according to the invention can be an optical, acoustic, magnetic or other sensor.

According to a preferred embodiment, the sensor is an acoustic resonator as known from U.S. Pat. No. 7,468,608 B2 and DE 103 08 975 B4. In addition, a reservoir (in particular a porous reservoir) is arranged on the described structure, in particular on the surface section (8), wherein the membrane is then applied onto this. In particular, it is then possible to detect a change in the viscosity, or an associated change in the penetration depth of acoustic waves.

The reservoir and the membrane can be applied equally well to test panels for QCM-D or OWLS technologies. In particular, the expansion or contraction of the PEM can be detected in this way.

DETAILED DESCRIPTION OF THE INVENTION

Figure 1:
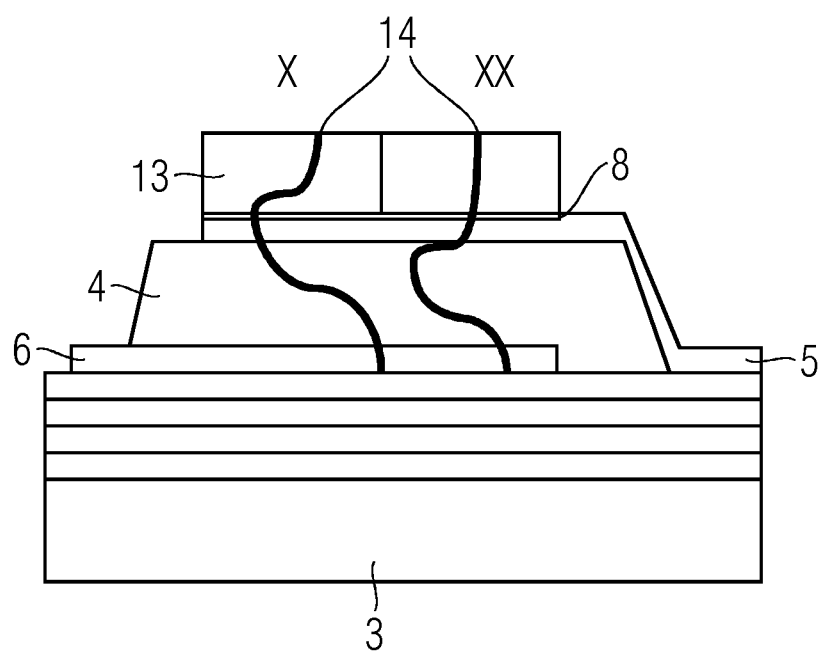
FIG. 1 shows the structure of an acoustic resonator in accordance with the invention.

Referring now to the figures of the drawing in detail and first, particularly, to FIG. 1 thereof, there is shown structure according to the above-mentioned U.S. Pat. No. 7,468,608 B2 and German patent DE 103 08 975, in particular the substrate 3 featuring e.g. an acoustic mirror for amplification of the signal, on top of which is the first electrode 6, the piezoelectric layer 4, the top electrode 5 and the surface section 8. According to the invention, provision is made for an additional layer 13 on the surface section or test panel 8, wherein said additional layer 13 is unfilled (i.e. the substance to be detected is not present) on the left-hand side (X) and is filled by the substance to be detected on the right-hand side (XX).

The figure schematically shows the course of the acoustic wave 14, which clearly penetrates into the layer 13 in the case of X (the unfilled reservoir), whereas the acoustic wave has almost disappeared in the filled reservoir (XX). This shows that the acoustic wave does not penetrate as far into the filled reservoir XX as it does in the unfilled reservoir X.

Figure 2:
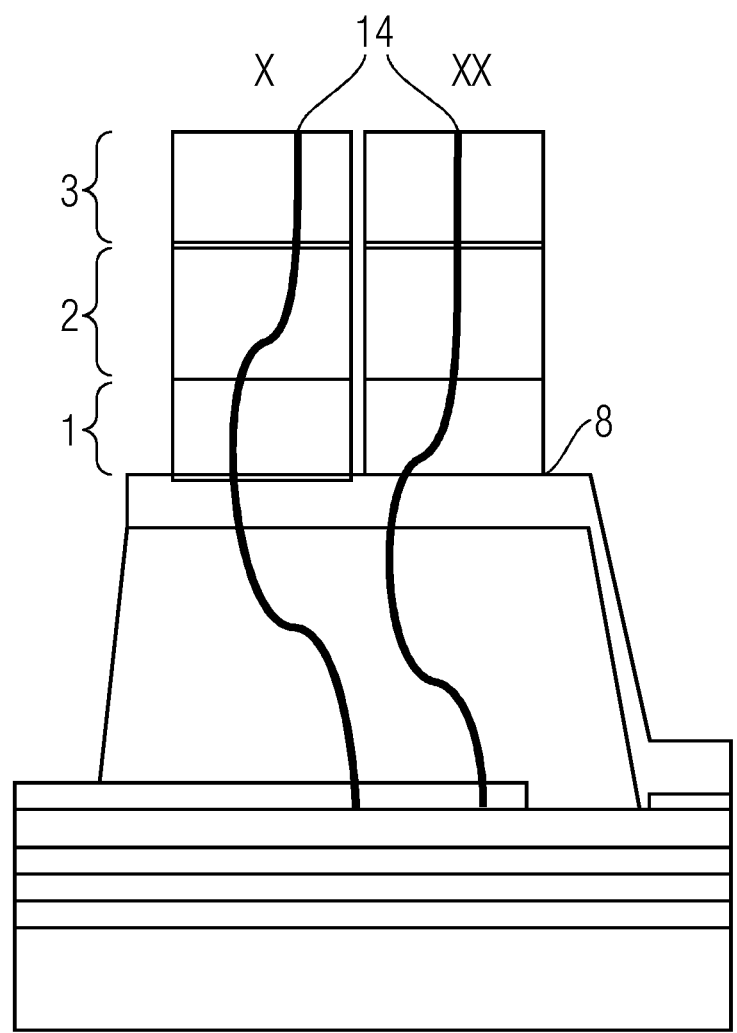
FIG. 2 shows the same embodiment, wherein the test panel is magnified beyond its true dimensions.

This effect can be seen more accurately in FIG. 2. The structure that is familiar from FIG. 1 is evident again, though here the course of the acoustic wave is shown more clearly. The wave arrives through the top electrode in the test panel 8, where it continues as a wave as far as the center of the layer in the case of X (the unfilled reservoir), whereas it penetrates no further than into the bottom third of the layer in the case of the reservoir XX, which is filled with the substance to be detected.

Figure 3:
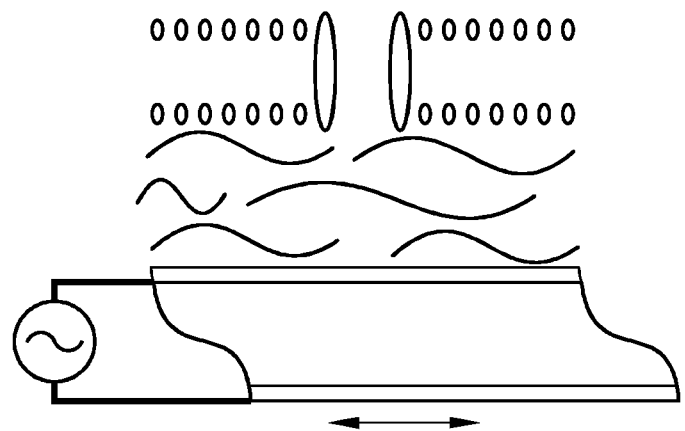
FIG. 3 shows a further embodiment with acoustical sensor.

FIG. 3 shows a further embodiment with an acoustical sensor. On a substrate 3 which may comprise quartz Crystal Microbalance crystals (QCM-D) is a reservoir 13 in form of a PEM-multilayer arranged. On the PEM-layer 13 there is a cell-membrane 7 arranged. The PEM layer may be an ion selective membrane. The membrane can be a part of cells, cell fractures, lipid bilayers. The reservoir 13 between the membrane 7 and the substrate 3 takes the substance which is to be detected e.g. a drug and swells or contracts depending on the interaction of the PEM and the drug. The difference in the reservoir 13 may be measured by the change of the acoustical signal in the substrate 3.

Figure 4:
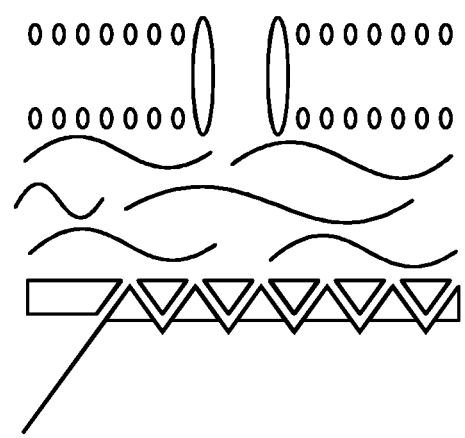
FIG. 4 shows a further embodiment with optical sensor.

A further implementation is shown in FIG. 4: there, light is injected into an optical wave guide.

As the composition of the material in the reservoir 13 is changing, the optical properties of the reservoir 13 are changing, too, and hence the light path in the reservoir 13 and wave guide 10 changes. Analysis of the light path in the wave guide 10 thus allows the drawing of conclusions about the materials in the reservoir 13.

The acoustic resonator can detect the difference in the acoustic permeability of the filled and unfilled material. This is possible because in one case (X) the mass of the layer of the central third is detected by the sensor and therefore contributes to the change in the resonance frequency, while in the other case (XX) the mass of the central third of the layer is not penetrated by the acoustic wave and therefore does not contribute to a shift in the resonance frequency.

The substance to be detected changes the permeability of the acoustic wave, for example.

This change in the acoustic permeability follows the regularity represented by the following formula:

$$\delta = \sqrt{2\eta/\rho\omega}$$

where
$\eta$=viscosity
$\rho$=density
$\omega$=angular frequency.

The sorbed substance therefore changes the viscosity and hence the permeability for acoustic waves, and consequently results in a frequency change because the mass of the reservoir that is not traversed in the filled reservoir is directly proportional to the signal change.

The thickness of the layer 13, i.e. the reservoir including the membrane, is preferably greater than the penetration depth of the acoustic wave, in order to ensure that additional masses, e.g. particles that are adsorbed in a non-specific manner such as dirt, do not contribute to the measured signal.

Depending on their state of aggregation, the examined substances can be detected in liquid form, gaseous form, or even as a solution of solid compounds.

The present invention enables small and extremely small molecules, including ions or atoms, to be detected in an exceptionally sensitive manner. This occurs in a simple manner by means of the known acoustic resonator FBAR or by means of other technologies that measure the physical properties of the filled layer. The permeability of substances (e.g. active ingredients) through membranes such as cell membranes, lipid bilayers, and cell walls can be examined by combining a sensor with the reservoir and the membrane.

The invention claimed is:

1. A biochip, comprising:

a sensor and a test panel disposed on said sensor;

said sensor being an acoustic resonance sensor with a first electrode disposed on a substrate, a piezoelectric layer disposed on said first electrode, and a second electrode disposed on said piezoelectric layer; and;

said test panel being disposed on said second electrode and having a reservoir formed of an absorbent layer and a membrane on top of said absorbent layer, said reservoir being a multilayer polymer and said membrane being at least one membrane selected from the group consisting of a lipid bilayer, a cell, a cell wall, and a cell membrane;

wherein a thickness of said reservoir and said membrane is greater than a penetration depth of an acoustic wave; and wherein said sensor is configured to measure a permeability of a substance to be detected through said membrane.

2. The biochip according to claim 1, wherein said reservoir comprises a porous material.

3. The biochip according to claim 1, wherein a permeability of said membrane is adapted to the substance to be detected.

4. The biochip according to claim 1, wherein said reservoir is made of a material selected from the group consisting of polymers, gels, porous ceramic materials and porous metallic materials.

5. The biochip according to claim 1, wherein said sensor is at least one sensor selected from the group consisting of acoustic sensors, optical sensors, magnetic sensors, and mechanical sensors.

6. The biochip according to claim 1, wherein said membrane on said reservoir is composed directly of cells or lipid bilayers.

7. The biochip according to claim 1, which comprises proteins provided within said membrane for influencing a permeability of said membrane.

8. The biochip according to claim 1, wherein said sensor is configured to react to a change in an optical property of said test panel.

9. The biochip according to claim 1, wherein said reservoir comprises a polyelectrolyte multilayer polymer.

10. The biochip according to claim 9, wherein said polyelectrolyte multilayer polymer contains polyelectrolytes selected from the group consisting of polyetherimide (PEI), polyallylamine (PAH), polyglutamic acid (PGA), and polystyrol sulfonate (PSS).

11. The biochip according to claim 1, wherein said reservoir is a dual reservoir including an unfilled reservoir portion and a filled reservoir portion adjacent said unfilled reservoir portion, wherein said filled reservoir portion is filled with the substance to be detected and said unfilled reservoir portion is not filled with the substance to be detected, and wherein said sensor is configured to detect an acoustic wave traversing said unfilled reservoir portion and an acoustic wave traversing said filled reservoir portion.

* * * * *